(12) United States Patent
Duez et al.

(10) Patent No.: US 6,405,438 B1
(45) Date of Patent: Jun. 18, 2002

(54) ANTICHAFING STRIP FOR SHAVING EQUIPMENT HEAD AND SHAVING EQUIPMENT HEAD COMPRISING SAME

(75) Inventors: José Duez, Boulogne sur Mer; Jean Rebaudieres, Compiegne, both of (FR)

(73) Assignee: Societe Bic, Clichy (FR)

(*) Notice: Subject to any disclaimer, the term of this patent is extended or adjusted under 35 U.S.C. 154(b) by 0 days.

(21) Appl. No.: 09/529,337
(22) PCT Filed: Oct. 15, 1998
(86) PCT No.: PCT/FR98/02215
§ 371 (c)(1), (2), (4) Date: Jun. 28, 2000
(87) PCT Pub. No.: WO99/19124
PCT Pub. Date: Apr. 22, 1999

(30) Foreign Application Priority Data

Oct. 15, 1997 (FR) .............................. 97 13132

(51) Int. Cl.[7] .............................................. B26B 21/44
(52) U.S. Cl. ............................................... 30/41
(58) Field of Search ..................... 30/41; 427/430.1; 424/73

(56) References Cited

U.S. PATENT DOCUMENTS

| | | |
|---|---|---|
| 3,154,514 A | 10/1964 | Kelley, Jr. |
| 3,181,973 A | 5/1965 | Duddy |
| 3,984,566 A | 10/1976 | Van Scott et al. |
| 4,170,821 A | 10/1979 | Booth ........................... 70/41 |
| 4,182,582 A | 1/1980 | Youval et al. |
| 4,234,599 A | 11/1980 | Van Scott et al. |
| 4,381,293 A | 4/1983 | Michel |
| 4,451,482 A | 5/1984 | Cagen |
| 4,624,051 A | 11/1986 | Apprille, Jr. et al. |
| 4,734,276 A | 3/1988 | Ziegler |
| 4,778,640 A | 10/1988 | Braun et al. |
| 4,850,106 A | 7/1989 | Braun et al. |
| 4,872,263 A | 10/1989 | Etheredge, III |
| 4,875,287 A | 10/1989 | Creasy et al. ........................... 30/41 |
| 5,056,221 A | * 10/1991 | Thoene ........................... 30/41 |
| 5,095,619 A | 3/1992 | Davis et al. |
| 5,113,585 A | 5/1992 | Rogers et al. |
| 5,349,750 A | 9/1994 | Tseng |
| 5,430,939 A | 7/1995 | Johnston |
| 5,454,164 A | 10/1995 | Yin et al. |
| 5,551,152 A | 9/1996 | Tseng |
| 5,626,154 A | 5/1997 | Rogers et al. |
| 5,692,302 A | 12/1997 | Martin et al. |
| 5,713,131 A | 2/1998 | Rogers et al. |
| 6,149,981 A | * 11/2000 | Chadwick et al. ....... 427/430.1 |

FOREIGN PATENT DOCUMENTS

| | | |
|---|---|---|
| FR | 2410541 | 6/1979 |
| GB | 2 024 082 A | 1/1980 |
| WO | WO 92/15292 | 9/1992 |
| WO | WO 93/10776 | 6/1993 |

* cited by examiner

Primary Examiner—Hwei-Siu Payer
(74) Attorney, Agent, or Firm—Pennie & Edmonds LLP

(57) ABSTRACT

The anti-friction strip of the invention for a discardable razor is obtained by extruding a polymer mixture comprising an insoluble polymer material and polyethylene oxide. It has an initial coefficient of dynamic friction ($K_D$) of the order of or less than 0.2. The mixture for extrusion includes, as its polyethylene oxide, only a substance whose mean molecular weight is greater than 3.5 million. The strip is preferably obtained by extruding a mixture comprising polystyrene and polyethylene oxide having a mean molecular weight greater than 4 million, and in particular a single polyethylene oxide having a molecular weight greater than 7 million. The invention also provides a shaving head having the above-specified anti-friction strip fixed thereto by ultrasonic welding.

18 Claims, 1 Drawing Sheet

Figure 1:
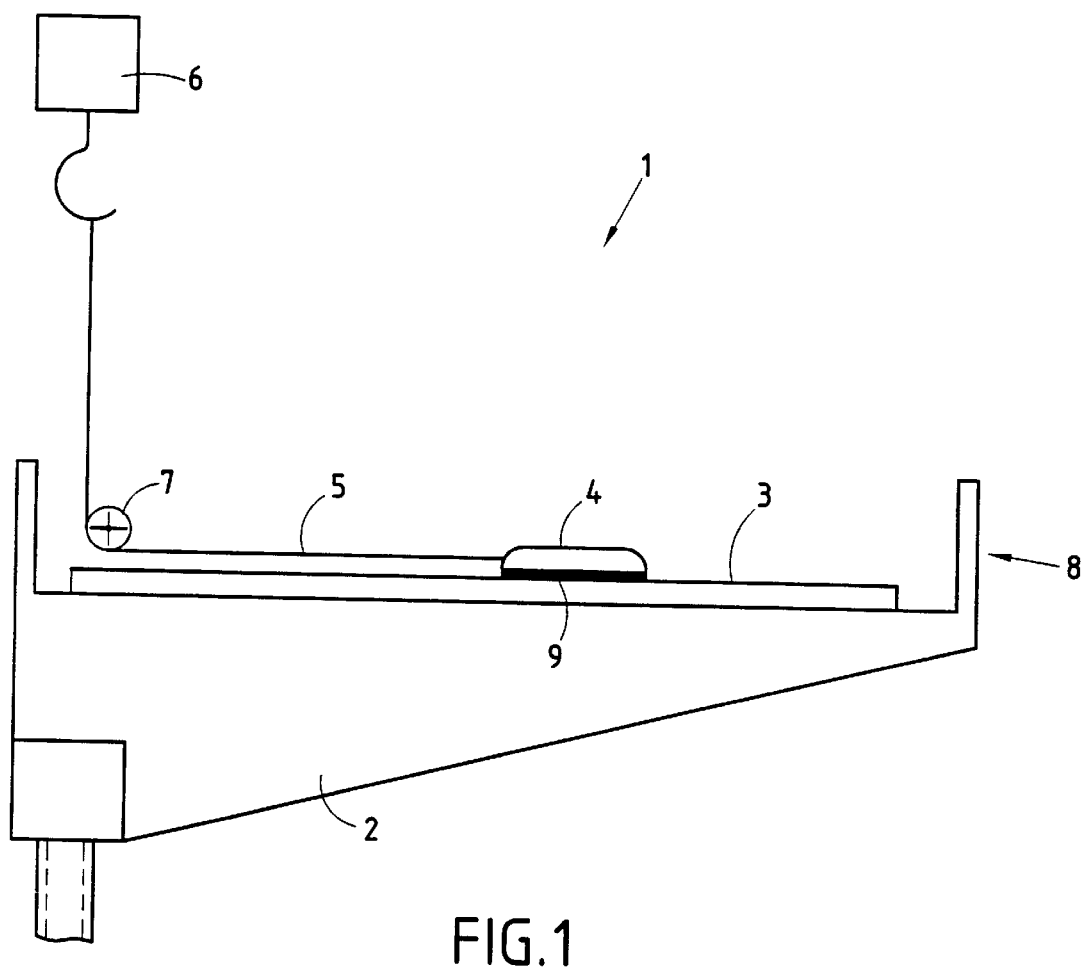

ANTICHAFING STRIP FOR SHAVING EQUIPMENT HEAD AND SHAVING EQUIPMENT HEAD COMPRISING SAME

BACKGROUND OF INVENTION

1. Field of Invention

The present invention relates to the field of shaving by mechanical means using a discardable razor; it relates more particularly to an auxiliary shaving article in the form of a strip and referred to as a "strip", which is fixed on the shaving head, preferably in the vicinity of the shaving blades, and which contains at least one shaving-assistance component that is soluble in water.

2. Description of the Related Art

When the razor is used, the user dips the shaving head in hot water, thereby making a portion of the shaving-assistance components) accessible and leachable, which components come into contact with the skin on each pass of the razor.

In U.S. Pat. No. 4,170,821 to Booth, the auxiliary shaving article proposed is combined with a micro-encapsulating or micro-porous water-soluble solid structure for retaining the shaving-assistance component which can be selected from a list of substances comprising a lubricant for reducing the effect of friction between the razor and the skin, an agent for reducing rubbing between the razor and the skin, an agent suitable for modifying hair structure, a cleansing agent, a pharmaceutical agent, a cosmetic agent, and a coagulation agent. As an example of a lubricant for reducing the effect of friction between the razor and the skin, U.S. Pat. No. 4,170,821 cites a micro-encapsulated silicone-based oil, and as an example of an agent for reducing rubbing between the razor and the skin, that document cites an oxide of polyethylene having molecular weight lying in the range 100,000 to 6,000,000, a non-ionic polyacrylamide, and a natural polysaccharide derived from plant matter such as guar gum.

In document EP-B-0 1 184 440, provision is made to form an auxiliary shaving article in the form of a strip by extruding a mixture of water soluble and insoluble polymer materials. That document gives a list of water soluble polymers comprising polyethylene oxide, polyvinylpyrrolidone, polyacrylamides, hydroxypropylcellulose, polyvinylimidazoline, and hydroxyethyl polymethacrylate. In a particular embodiment, the mixture for forming said strip by extrusion is made up of 20% by weight water insoluble polystyrene and 80% by weight of a mixture of polyethylene oxide comprising 60% "coagulating polyox" polyethylene oxide of molecular mass equal to 5,000,000, and 40% "WSR N-750 polyox" polyethylene oxide of molecular mass equal to 300,000. No explanation is given in that document concerning the advantage of mixing those two types of polyethylene oxide together, other than for obtaining a mean molecular weight of about 3.5 million for the polyethylene oxide in the final mixture.

In document EP-B-0 550 605, the mixture for forming the auxiliary shaving article by extrusion in the form of a strip contains, in addition to the water soluble and insoluble materials, an agent of low molecular weight for amplifying the release of the water soluble polymer material making up the shaving-assistance component. Amongst all of the possible examples, that document cites polyethylene oxide as a shaving-assistance component which can be leached by water, and polyethylene glycol as an agent for amplifying release. In characteristic manner, according to that document EP-B-0 550 605, the mixture for forming the auxiliary shaving article by extrusion in the form of a strip comprises 20% to 60% by weight of insoluble polymer material that forms the matrix of the strip, 20% to 75% by weight of water soluble polymer material that constitutes the water-leachable shaving-assistance component, and 5% to 20% by weight of agent for amplifying release. In all of the examples cited in that document, exactly the same mixture of two types of polyethylene oxide is to be found as already described in prior document EP-B-0 184 440, i.e. 60% by weight of coagulating polyox and 40% by weight of WSR N-750 polyox. In the examples cited, the agent for amplifying release is a polyethylene glycol of molecular weight lying in the range 4,500 to 20,000. The intended purpose of having the release-amplifying agent present is to make it possible to maintain a sufficient quantity of insoluble polymer for retaining sufficient mechanical strength in the extruded strip both on initial manufacture and assembly, and after a significant quantity of water soluble material has already been leached, while still making it possible for a sufficient quantity of water soluble shaving component to be released to provide effective shaving assistance throughout the total useful lifetime intended for the blade or blades.

In that document EP-B-0 550 605, no explanation is given concerning the reasons which enable certain specified agents of low molecular weight to amplify release of the shaving-assistance component, i.e. ethylene glycol, methoxy polyethylene glycol, methyl-cellulose, and carboxypolymethylene. It should be observed that those four examples are the only examples mentioned in that document, and that they all relate to the above-mentioned mixture of polyethylene oxide and the added polyethylene glycol. It should be recalled that polyethylene oxide and polyethylene glycol have the same general formula, differing only in method of manufacture and mean molecular weight. The term "polyethylene glycol" is used to designate a compound whose molecular weight is generally less than 20,000. The term "polyethylene oxide" is used to designate a compound whose main molecular weight is greater than 100,000, it being understood that a very wide variety of products are available on the market, having the general formula of polyethylene oxide, with mean molecular weights lying in the range 100,000 to 8,000,000.

Thus, according to the Applicant, it can be thought that polyethylene glycol is used in document EP B 0 550 605 also as a shaving-assistance component, in addition to the low molecular weight polyethylene oxide (WSR N-750 polyox) so as to obtain sufficient release of shaving-assistance components during the lifetime of the discardable shaving head.

Thus, present trends in this field are towards releasing a large amount of shaving-assistance soluble component, in particular polyethylene oxide which is preferably associated with polyethylene glycol. Nevertheless, because a large amount is released, the component remains present on surfaces of the skin that have already been shaved, and can form a film by drying out. To avoid that drawback, it is necessary for the user to wash after shaving. However, depending on the quality of the water available, this removal is not always satisfactory and a sticky feeling can remain on the skin. If all or some of the soluble component remains on the skin, that can be a source of irritation, particularly for sensitive skins.

To mitigate those drawbacks, proposals have already been made in document EP-B-0 321 679, for a solution that is different in principle since it avoids the use of a soluble polymer by proposing to implement a xerophilic gel as the anti-friction agent which, while absorbing water as a dispersing agent, becomes transformed into a lyophilic gel having very great aptitude for sliding on the skin of the user, with a coefficient of friction $\mu$ of less than 0.25. By adding the dispersion agent, e.g. water, the xerophilic gel becomes transformed once more into a lyophilic gel by swelling, with its outside surface becoming slippery and presenting a low coefficient of friction. During this stage, the colloidal substance forming the-lattice of the lyophilic gel does not pass into solution, thereby making it possible to avoid forming on the skin a film constituted by a shaving-assistance component extracted from the strip, as was the case in the previously-cited documents.

Nevertheless, according to the teaching of that document EP-B-0 321 679, it is necessary to put the coating that forms the xerophilic gel on a support strip in order to constitute the anti-friction strip proper for placing on the shaving head. The materials recommended for forming the xerophilic gel do not withstand temperatures that would make it possible to consider fabricating the anti-friction strip by extrusion.

SUMMARY OF INVENTION

The object of the Applicant is to propose another solution that does not make use of a xerophilic gel, that makes it possible to obtain an anti-friction strip by extrusion, while enhancing ability to slide on the skin of the user, and without running the risk of forming a film of the soluble component on the user's skin.

DETAILED DESCRIPTION OF INVENTION

This object is achieved in full by the anti-friction strip for discardable razors of the invention which, in conventional manner, is obtained by extruding a polymer mixture of an insoluble polymer material and of polyethylene oxide as the soluble polymer material. In manner characteristic of the invention, said strip is characterized by an initial coefficient of dynamic friction ($K_D$) of the order of or less than 0.2, and by the fact that the mixture to be extruded comprises, as its polyethylene oxide, only a substance whose mean molecular weight is greater than 3.5 million.

The Applicant has observed that the presence of polyethylene oxide of lower molecular weight, even when mixed with polyethylene oxide of higher molecular weight, leads to an increase in the coefficient of dynamic friction.

It also turns out that the greater the molecular weight of the polyethylene oxide, the smaller its solubility in water. Thus, with a polyethylene oxide of molecular weight greater than 3.5 million, release is obtained that is relatively low compared with the figures given in documents EP-B-0 184 440 and EP-B-0 550 605. The risk of skin irritation or of the sensation of slippery skin is thus greatly reduced or even eliminated by this fact.

During comparative shaving tests, the Applicant has also observed another significant technical advantage in using only a polyethylene oxide of high molecular weight in the mixture, namely that of retaining sliding capacity for the anti-friction strip which remains substantially constant or which varies relatively little during a series of shaves using the same strip. By way of comparison, an anti-friction strip including polyethylene oxide of lower molecular weight presents a significant drop in its sliding capacity after two or three shaves, thereby giving rise to a sensation that is quite disagreeable for the user.

Preferably, with reference to this technical advantage, the anti-friction strip is obtained by extruding a mixture of polystyrene and a polyethylene oxide of mean molecular weight that is greater than 4 million.

Another problem which the Applicant has sought to resolve lies in fixing the anti-friction strip to the shaving head. In document FR-A-2 410 541, the strip is fixed to the shaving head, preferably in a housing provided for that purpose. No indication is given as to how it is fixed therein. In document EP-B-0 184 440, the strip has a special profile, and it is locked in position by structural elements on the shaving head. That solution makes fabrication of the head more complex. In document EP-B-0 550 605, the anti-friction strip is fixed by means of adhesive in a hollow portion of the shaving head. That solution requires the use of an adhesive that sets particularly quickly if a high rate of manufacturing throughput is to be obtained.

In order to fix the anti-friction strip on the shaving head, the Applicant proposes the well-known technique of ultrasonic welding. This technique consists in creating vibratory conditions under the action of ultrasound that make it possible, locally, to raise the temperature of two touching plastics materials so as to obtain localized interpenetration of the two materials.

The Applicant has observed that by using the ultrasonic welding technique with an anti-friction strip of polyethylene oxide having a molecular weight greater than 3.5 million makes it possible to obtain a weld that is of good quality. A weld between a first plastics material acting as a base and a plastics material applied thereto is said to be of "good quality" when breaking the weld by applying mechanical stress gives rise to breakage taking place for the most part in the base material or in the material applied thereto, but not within the weld proper. Material is, so to speak, torn beyond the zone in which the two materials have interpenetrated.

Best results have been obtained with an anti-friction strip made by extruding a mixture of poly-ethylene and a polyethylene oxide having a mean molecular weight in excess of 7 million, which is fixed by ultrasonic welding onto a portion of a shaving head that is made of polystyrene.

The present invention will be better understood on reading the following description of an embodiment of an anti-friction strip having a low dynamic friction coefficient, made by extruding a mixture of polystyrene and of polyethylene oxide having a mean molecular weight greater than 3.5 million, and shown in the sole figure of the accompanying drawing which is a diagram of test apparatus for determining the coefficient of dynamic friction.

To determine the slidability of the anti-friction strip of the invention, the Applicant has adapted registered French standard NF T54–112. The purpose of that standard is to measure static and dynamic coefficients of friction between plastics sheets when sliding on one another or on other substances. In the present case, the first plastics sheet is constituted by the anti-friction strip of the invention, and the second sheet, referred to below as the "sliding track", is made of a material whose characteristics are close to those of skin, e.g. a sheet of polyurethane, a covering of polyurethane and polyester (product referenced 4PE100/B09T, sold by Catry), or a sheet of acid catalysed melamine (sold under the trademark Velleda). Naturally the exact value of the coefficient of dynamic friction is a function of the material used for the sliding track.

The coefficient of dynamic friction ($K_D$) is the ratio of the traction force that needs to be exerted to maintain sliding between the two surfaces over the normal force urging the two surfaces against each other. To calculate this coefficient, the force required for starting displacement and the force required for maintaining displacement are measured relative to each other when the two materials are in contact and the contact pressure between the two materials is kept constant during the test.

The apparatus 1 implemented for performing this test was constituted by a horizontal support 2 which is designed to support the sliding track 3, e.g. a sheet of polyurethane that was 30 cm long and 15 cm wide, together with a steel slug 4 having a mass of 198 g, a length of 6.35 cm, and a width of 3.4 cm. A sample 9 of anti-friction strip to be tested was placed beneath the slug 4 in contact with the sliding track 3. The slug 4 was pulled by a cable 5 connected to a dynamometer 6, a difflector pulley 7 enabling the slug 4 to be moved horizontally. The support 2 constituted the bottom of a vessel 8 that was thermostatically controlled and that contained water heated to 42° C., the quantity of said water being sufficient to form a film between the sliding track 3 and the sample of anti-friction strip 9 under test.

The slug was moved together with its sample in rectilinear manner along the sliding track at a speed of 150 mm per minute ±15 mm per minute over a distance of 12 cm. Ten tests were performed per sample. The mean force necessary for maintaining displacement of the slug 4 was measured. The coefficient of dynamic friction ($K_D$) is the ratio of that force over the weight of the assembly constituted by the slug 4 plus the sample 9.

The value of the dynamic coefficient ($K_D$) in question is the initial value obtained during the first test. The value of the coefficient varied when performing a series of tests separated by periods during which the strip was dried. It was also observed that it varied less when, after ten tests had been performed so that a mean could be obtained, the strip was rinsed abundantly. Similarly, it was preferable to clean or even replace the sliding track between two tests.

By implementing the above method, the Applicant performed comparative tests between anti-friction strips, all made by extruding a mixture of polystyrene and polyethylene oxide of various molecular weights.

All of the tests performed showed that the presence in the mixture of polyethylene oxide of low molecular weight, and in particular about 300,000, on its own or in the presence of polyethylene glycol, gives rise to a sticking phenomenon that impedes sliding.

In contrast, in accordance with the invention, initial coefficients of dynamic friction of the order of or less than 0.2 were obtained by using polyethylene oxides having a mean molecular weight greater than 3.5 million, which coefficients characterize good sliding without the sticking phenomenon.

Comparative tests that were more subjective but closer to shaving conditions were also developed by the Applicant. The two anti-friction strips to be compared were stuck to a support plate, with the two strips being parallel and spaced apart from each other by a distance of about two to three centimeters. The tests comprised two operations that were repeated several times in succession and then the set of tests was repeated on several days in a row: the first operation consisted in plunging the plate into warm water (about 40° C. to 42° C.) thus simulating putting the razor under hot water from the tap; the second consisted in rubbing both strips simultaneously against two fingers of the same hand, thus simulating a shaving sequence. The various times required for each operation were given to each test. In a first example, the first operation lasted 15 seconds and the second 1 minute, with both operations being performed in succession, twice in all. In the second example, the first operation lasted 5 seconds and the second 30 seconds, both operations being performed in succession four times in all. The set constituted by repeating those two operations was performed several days in a row, e.g. 6 or 7 days, simulating the lifetime of a discardable razor.

The sliding sensation perceived simultaneously on the two fingers made it possible to classify the strips relative to each other, in terms of sliding ability, and to assess the difference in sliding between the two strips. In particular, by means of those tests, which reproduced real shaving conditions quite closely, the Applicant was able to observe that an anti-friction strip obtained by extruding a polymer mixture comprising polystyrene and a polyethylene oxide of the Alkox 300 type has sliding capacity which is always better than that of a publicly-available strip obtained under the same conditions but using a mixture of polyethylene oxide and of polyethylene glycol; furthermore, it is remarkable that this difference becomes greater with increasing number of simulated shaving sequences.

With the anti-friction strip of the invention, there is a small decrease in sliding capacity that is fairly regular from one day to the next, whereas with the above-mentioned public-domain strip, a like decrease occurs, but on the third or fourth day, there is a sudden drop in sliding capacity.

For fixing the anti-friction strips of the invention on shaving heads, the Applicant recommends using the ultrasonic welding technique. In order to verify the quality of ultrasonic welds between polystyrene and polyethylene oxide, polystyrene plates were welded to plates extruded from a mixture of 60% polyethylene oxide and 40% polystyrene. To verify the quality of the welding, the plate extruded from polystyrene and polyethylene oxide was fixed in a vice, the pure polystyrene plate was taken hold of, and traction was applied to breakage. Either the break took place through the weld proper, or else the break took place in the plate of polystyrene and polyethylene oxide. A weld is generally considered to be of good quality if the major part of the break takes place in the plate and not in the weld.

The table below gives the results obtained with the above-mentioned Alkox 160, 240, and 300 products. An additional test was performed using Alkox E 100 whose molecular weight as specified by the manufacturer lies in the range 2.5 million and 3 million. As can be seen, with Alkox E 100, the quality of the weld is less good insofar as all of the breaks are located in the weld proper and not in the material. Furthermore, there is a very large difference as to the mean force in kilograms weight required to break the strip obtained from Alkox E 30 100 compared with the mean forces required for Alkox E 160, E 240, and E 300, which give results that are very close to one another. The best results concerning coefficient of dynamic friction and concerning suitability for ultrasonic welding were obtained with the anti-friction strip made by extruding a mixture of 40% by weight polystyrene and 60% by weight polyethylene oxide having a molecular weight lying in the range 7 million to 8 million, said strip being ultrasonically welded to a shaving head made of polystyrene.

| Type of polyethylene oxide | Mean force (kg) | Number of breaks in the weld (on 4 samples) |
| --- | --- | --- |
| Alkox E 100 | 12.9 | 4/4 |
| Alkox E 160 | 20.8 | 2/4 |
| Alkox E 240 | 21.6 | 1/4 |
| Alkox E 300 | 21.67 | 0/4 |

The preferred anti-friction strip of the invention which gives the best results both in terms of sliding capacity and durability of said capacity, and also in terms of manufacturing quality, is a strip which is obtained by extruding a polymer mixture having about 30% polystyrene and about 70% polyethylene oxide with a mean molecular weight of more than 7 million. The extruded mass is more compact than with polyethylene oxides of lower molecular weight, thus making it possible to obtain a strip whose profile is more accurate and more regular.

In a preferred embodiment, using Alkox 300 (mean molecular weight in the range 7 million to 8 million), the mixture comprised 66.5% Alkox 300, 32% polystyrene, and 1.5% additives, in particular colored pigments.

In addition to the above-mentioned characteristic polymer materials, the anti-friction strip of the invention can naturally also contain shaving additives, in particular those mentioned in U.S. Pat. No. 4,170,821: cleaning agents, pharmaceutical agents, cosmetic agents, and coagulating agents.

What is claimed is:

1. An anti-friction strip for a discardable razor, the strip being obtained by extruding a polymer mixture comprising an insoluble polymer material and polyethylene oxide, the strip being characterized by an initial coefficient of dynamic friction ($K_D$) of the order of or less than 0.2, and by the fact that the mixture to be extruded comprises, as its polyethylene oxide, only a substance whose mean molecular weight is greater than 3.5 million.

2. An anti-friction strip according to claim 1, characterized in that it is obtained by extruding a mixture comprising polystyrene and a polyethylene oxide having a mean molecular weight greater than 4 million.

3. A shaving head having an anti-friction strip according to claim 2 fixed thereto by ultrasonic welding.

4. An anti-friction strip according to claim 2, characterized in that it is obtained by extruding a mixture of polystyrene and a single polyethylene oxide having a molecular weight greater than 7 million.

5. A shaving head having an anti-friction strip according to claim 4 fixed thereto by ultrasonic welding.

6. An anti-friction strip according to claim 4, characterized in that it is obtained by a mixture of about 30% polystyrene and about 70% of a single polyethylene oxide having a molecular weight greater than 7 million.

7. An anti-friction strip according to claim 6, wherein the polymer mixture comprises 40% polystyrene and 60% polyethylene oxide and wherein the polyethylene oxide has a molecular weight lying in the range of 7 million to 8 million.

8. A shaving head having an anti-friction strip according to claim 6 fixed thereto by ultrasonic welding.

9. An anti-friction strip according to claim 6, characterized in that it is obtained from a mixture of 32% polystyrene, 66.5% polyethylene oxide having a molecular weight lying in the range 7 million to 8 million, and 1.5% additive.

10. An anti-friction strip according to claim 9, wherein the additive comprises a colored pigment.

11. A shaving head having an anti-friction strip according to claim 9 fixed thereto by ultrasonic welding.

12. A shaving head having an anti-friction strip according to claim 1 fixed thereto by ultrasonic welding.

13. A shaving head according to claim 12, in which the portion on which the anti-friction strip is fixed is made of polystyrene.

14. An anti-friction strip according to claim 1, wherein the polymer mixture further comprises a shaving additive.

15. An anti-friction strip according to claim 14, wherein the shaving additive is a cleaning agent.

16. An anti-friction strip according to claim 14, wherein the shaving additive is a pharmaceutical agent.

17. An anti-friction strip according to claim 14, wherein the shaving additive is a cosmetic agent.

18. An anti-friction strip according to claim 14, wherein the shaving additive is a coagulating agent.

* * * * *